United States Patent [19]

Huryn et al.

[11] Patent Number: 5,126,347
[45] Date of Patent: Jun. 30, 1992

[54] ISOMERIC DIDEOXYNUCLESIDES

[75] Inventors: Donna M. Huryn, Newtown, Pa.; Steve Yik-Kai Tam, West Caldwell; Manfred Weigele, Clifton, both of N.J.

[73] Assignee: Hoffmann-La Roche Inc., Nutley, N.J.

[21] Appl. No.: 309,561

[22] Filed: Feb. 13, 1989

[51] Int. Cl.⁵ .................. A61K 31/52; C07D 473/18; C07D 473/34
[52] U.S. Cl. ..................... 514/262; 514/266; 544/276; 544/277; 544/320; 549/22; 549/475; 549/480; 536/54
[58] Field of Search ............. 544/276, 277; 514/265, 514/266, 262

[56] References Cited

U.S. PATENT DOCUMENTS

| | | | |
|---|---|---|---|
| 4,772,606 | 9/1988 | Sircar et al. | 514/262 |
| 4,788,181 | 11/1988 | Driscoll et al. | 514/49 |
| 4,916,224 | 4/1990 | Vince et al. | 544/254 |

FOREIGN PATENT DOCUMENTS 0098099 6/1984 Japan ................. 544/277

OTHER PUBLICATIONS

Takano et al., *Heterocycles*, 16(6):951 (1981).
Hayashi et al., Proc. Natl. Acad. Sci., USA, vol. 85, pp. 6127-6131 (Aug. 1988).
Montgomery et al., J. Org. Chem., vol. 43(4), pp. 541-544 (1978).

*Primary Examiner*—Diana Rivers
*Attorney, Agent, or Firm*—George M. Gould; Bernard S. Leon; William H. Epstein

[57] ABSTRACT

Isomeric derivatives of 2',3'-dideoxyadenosine and 2',3'-dideoxyguanosine wherein the adenine or guanine base is attached to the 1' position of the iso-dideoxysugar residue by the 9-N position, the novel intermediates used in the synthesis of these compounds, and a method for treating a subject infected with a retrovirus by administering the compounds of the invention.

16 Claims, 3 Drawing Sheets

ISOMERIC DIDEOXYNUCLESIDES

TECHNICAL FIELD

The instant invention pertains to isomeric derivatives of 2',3'-dideoxyadenosine or 2',3'-dideoxyguanosine wherein the adenine or guanine base is attached through the 9-N position to the 1' position of the isodideoxy sugar residue, the pharmaceutically acceptable salts thereof, and pharmaceutical compositions containing these compounds.

The instant invention pertains to the novel intermediates used in the synthesis of the compounds of the invention.

The instant invention pertains to methods for synthesizing the compounds of the invention as well as methods for synthesizing the novel intermediates.

The instant invention also pertains to treating retroviral infections, particularly HIV, in subjects using the compounds of the invention.

BACKGROUND OF THE INVENTION

AIDS has become epidemic in modern times and the only therapeutics to date which have proven even partially successful are based upon inhibiting AIDS virus replication. One drug which has been approved for treating AIDS, 3'-azido-2',3'-dideoxythymidine (AZT), exhibits anti-AIDS activity primarily through inhibiting the viral enzyme reverse transcriptase. When AZT is administered to patients it is first phosphorylated to the triphosphate form by cellular kinases. The AZT triphosphate then acts as a terminator of the growing viral DNA chain as well as a reverse transcriptase inhibitor.

Other dideoxynucleosides such as 2',3'-dideoxyadenosine and 2',3'-dideoxyinosine also exhibit antiretroviral activity by inhibiting reverse transcriptase. The therapeutic use of these compounds is limited however, by their rapid degradation via hydrolysis of the sugar base linkage. The instant invention therefore comprises isomeric derivatives of 2',3'-dideoxynucleosides exhibiting a more stable nucleoside linkage.

SUMMARY OF THE INVENTION

The instant invention comprises isomeric derivatives of 2',3'-dideoxynucleosides of the following formula wherein A is 6-Amino-9H-purin-9-yl or 2-Amino-6-hydroxy-9H-purin-9-yl, wherein the amino group may be replaces by and N=CHR³R⁴, and R is OH or wherein $R^1$, $R^2$, $R^3$ and $R^4$ is each independently straight or branched chain $C_{1-20}$ alkyl, $C_{1-12}$ alkoxyalkyl, substituted or unsubstituted phenoxyalkyl ($C_{1-4}$), substituted or unsubstituted phenyl with the substituents selected from the group consisting of halogen, $C_{1-4}$ alkoxy, nitro, hydroxy, carboxyl or alkylamino, and the pharmaceutically acceptable salts thereof, and pharmaceutical compositions containing these compounds.

The instant invention also comprises the novel intermediates used in the synthesis of the compounds of the invention.

The instant invention is also directed to methods for synthesizing the compounds of the invention as well as methods for synthesizing the novel intermediates.

The instant invention is also directed to treating retroviral infections, particularly HIV, using the compounds of the invention.

| | Definitions |
| --- | --- |
| 1. lower alkyl | means an alkyl with 1-7 carbon atoms. |
| 2. halogen | means fluorine, chlorine, bromine, iodine. |
| 3. nucleobase | means any common base present in nucleosides such as adenine, guanine, cytosine, thymine, 2,6-diaminopurine, uracil, purine, 2-amino-purine, etc. |
| 4. AIBN | means a common radical initiator such as α,α'-azoisobutyronitrile. |
| 5. Leaving Group | means a functional group suitable for nucleophilic displacements such as alkyl or aryl sulfonates, activated O—H groups such as O—P̄Ph₃, halogens, etc. |
| 6. 18-Crown-6 | means a common phase transfer reagent such as 1, 4, 7, 10, 13, 16-hexaoxacyclooctadecane. |
| 7. "▼" | means that the residue is situated above the plane of the molecule. |
| 8. "⋮" | means that the residue is situated below the plane of the molecule. |
| 9. "ξ" | means that the residue may be situated above or below the plane of the molecule. |
| 10. masked precursor | means a chemical precursor of a specific functional group which is easily convertible to that functional group by some simple transformations. For example, acetals and esters are masked precursors of hydroxymethyl groups; aryl ethers and silyl ethers are masked precursors of hydroxy groups. |

DETAILED DESCRIPTION

Preferred is where A is unsubstituted 6-amino-9H-purin-9-yl, or unsubstituted 2-amino-6-hydroxy-9H-purin-9-yl.

Further preferred is where R is OH yielding the compounds:

Iso-dideoxyadenosine

IsoddA and

Iso-dideoxyguanosine

IsoddG and the pharmaceutically acceptable salts thereof as well as pharmaceutical compositions containing these compounds. The pharmaceutically acceptable salts may be salts of organic acids such as lactic, acidic, malic, or p-toluene sulfonic acid and the like as well as salts of pharmaceutically acceptable mineral acids such as hydrochloric, or sulfuric acid and the like.

The instant invention is also directed to the novel intermediates used in the synthesis of Compounds I and II.

The compounds of the invention may be prepared by beginning with a simple sugar derivative such as 1,2-O-methylethylidene-D-xylofuranose which, after a series of reactions is converted to a tosyl acetonide intermediate according to the following scheme:

In the above scheme 1,2-O-(1-methylethylidene)-α-D-xylofuranose is treated with tosyl chloride to yield 1,2-O-(1-methylethylidene)-5-O-p-(tolylsulfonyl)-α-D-xylofuranose. The compound obtained is then treated with 1,2-dichloroethane and thiocarbonyldiimidazole and results in the novel imidazole carbothioic acid derivative (Compound III) which, after treatment with tri-n-butyltin hydride and AIBN in toluene yields 3-Deoxy-1,2-O-(1-methylethylidene)-α-D-erythro-pentofuranose-4-methylbenzene-sulfonate. This tosyl acetonide may be then converted by either of two methods into a novel intermediate compound of the formula:

wherein B is $NH_2$, hydroxy, or any form of $NH_2$ or OH, any of their masked precursors, or a leaving group; and C is selected from the group consisting of hydroxymethyl or any of its masked precursors such as halomethyl, carboxylic acid, aldehyde, ester, acetal, thioacetal, alkoxymethyl, etc. This intermediate compound then serves as the basis for the synthesis of a wide variety of isomeric dideoxynucleosides including Compounds I and II.

This novel intermediate may be synthesized according to the following scheme:

The tosyl acetonide is treated with 1,2-propanedithiol and boron trifluoride etherate to yield the open chain diol. After purification the open chain diol V is stirred in a solution of methylene chloride and pyridine to generate the tetrahydrofuran IV(a) which is immediately reacted with tosyl chloride to generate the tosylated thioacetal IV(b). After purification of the tosylated thioacetal via flash column chromatography, conversion to the novel intermediate IV(c) is achieved by hydrolysis with mercuric chloride, then reaction with sodium borohydride. In this scheme Compounds IV(a), (b), (c), and V are novel intermediates.

Compound IV may also by synthesized according to the following scheme:

In this scheme reaction of the tosyl acetonide with an acetic acid/methanol solution yields a mixture of the methyl glycoside, the ring opened dimethylacetal, and the desired product, IV(d). After stirring this mixture for several days, complete conversion to the dimethylacetal tetrahydrofuran IV(d) is achieved. This unpurified compound is then tosylated under standard conditions to yield the dimethyl acetal, tosylate IV(e) which may be then converted to Compound IV(c) by acid hydrolysis and sodium borohydride reduction. In this scheme Compounds IV(d) and IV(e) are novel intermediates.

Compound IV may be then used to synthesize a variety of nucleosides including Compounds I and II via two basic strategies.

The first approach involves the direct displacement of a leaving group on the isodideoxy sugar by a nucleobase as illustrated in Equation 1. Synthesizing carbocyclic analogs of nucleosides (particularly adenine derivatives) according to this type of reaction has been reported in the literature, however, this method does not appear to be widely used.

Equation 1:

X = Leaving Group
Base-H = Nucleobase
C = CH$_2$OH or its masked precursor

The alternative classical method is based on the stepwise construction of the nucleobase. The synthesis of nucleosides, particularly purine and pyrimidine derivatives according to this methodology has been well documented in the literature. It is expected that all classical nucleobases could be incorporated into the isodideox- ynucleoside structure starting from the isodideoxysugar IV. The amino derivative, IV(f), is readily available from IV via standard chemical transformation so that the same intermediate may be used for either method. Compound IV(f) is a novel intermediate in Equation 2.

Equation 2:

X = Leaving Group
C = CH$_2$OH or its masked precursor

For example Compound I, isoddA, may be synthesized by treating Compound IV(c) with either of adenine, potassium carbonate, and a phase transfer reagent such as 18-crown-6; or with the sodium salt of adenine as set forth below.

Compound IV(e) may be used to synthesize Compound I according to the following scheme:

In the above scheme adenine, potassium carbonate, and 18-crown-6 are reacted with the dimethylacetal iso-sugar to yield the iso-ddA acetal VI. The dimethylacetal is then hydrolyzed to the aldehyde VII, using an oxalic acid solution. After neutralization the unstable aldehyde is immediately reduced by catalytic hydrogenation to iso-ddA, I. In this scheme Compounds IV(e), VI, and VII are novel intermediates.

Compound II may also be synthesized according to the general methods set forth above. Compound IV(c) is first reacted with Z-amino-6-chloropurine, a common phase transfer reagent such as 18-crown-6, and potassium carbonate to yield a novel 2-amino-6-chloropurineisodideoxynucleoside VII.

This compound is then converted to Compound II by either acidic or basic conditions, for example by heating in the presence of HCl:

In this scheme Compound VIII is a novel intermediate.

The isomeric dideoxynucleosides of the invention may also be synthesized according to the more classical methodology which involves formation of the nucleobase from an amine.

In the above scheme Compound IV(c) is reacted with sodium azide. The resulting compound is catalytically hydrogenated with Palladium on carbon to yield the corresponding amine, IV(f). Reaction of this amine with 5-amino-4,6-dichloropyrimidine in the presence of base yields the pyrimidine derivative IX, which in turn is converted to the purine adduct X by condensation with dimethoxymethyl acetate. This is followed by acid induced elimination to yield the 6-chloro purine isodideoxynucleoside X. A subsequent treatment with methanolic ammonia solution yields isoddA I along with XI. In this scheme Compounds IX, X, and XI are novel intermediates.

IsoddG can also be synthesized from compound IV(f) via a stepwise construction of the nucleobase as illustrated below. Reaction of IV(f) with 2-amino-6-chloro-4(3H)-pyrimidinone in the presence of triethylamine generates the pyrimidinone XII. Catalytic reduction of XII in the presence of Platinum oxide (PtO$_2$) yields the amino-pyrimidinone XIII. Treatment of XIII with triethylorthoformate and acid yields IsoddG, II. Compounds XII and XIII are novel intermediates.

The derivatives of Compound I and II which are substituted at the amino and hydroxy position may be easily made by reacting Compounds I and II with anhydrides represented by the general formula (ArCO)$_2$O, (ArCH$_2$CO)$_2$O, or (RCO)$_2$O wherein (ArCO)$_2$O represents aromatic anhydrides such as benzoic anhydride and (ArCH$_2$CO)$_2$O represents aralkyl anhydrides such as phenylacetic anhydride, and (RCO)$_2$O represents alkyl anhydrides. The product thus obtained will be the ester-amide derivatives of Compound I and II. Selective partial hydroysis of these derivatives with Triethylamine, or under alkaline conditions will yield the desired partially substituted Compounds I and II.

Compounds I and II are useful for treating a subject infected with a retrovirus, particularly HIV, by administering to the subject a virus inactivating effective amount of the compounds or their pharmaceutically acceptable salts.

Compounds I and II may be administered by any suitable route including orally, topically and parenterally including subcutaneous, intravenous, intramuscular or intradermal.

While it is possible for Compounds I and II to be administered alone it is preferably to present them as pharmaceutical formulations. The formulations of the invention comprise at least the Compound together with one or more acceptable carriers thereof and optionally other therapeutic agents. Each carrier must be "acceptable" in the sense of being compatible with the other ingredients of the formulation and not injurious to the patient. Formulations include those suitable for oral, and intraveneous administration. The formulations may conveniently be presented in unit dosage form and may be prepared by methods well known in the art of pharmacy.

Formulations of the present invention suitable for oral administration may be presented as discrete units such as capsules, cachets or tablets each containing a predetermined amount of Compounds I or II; as a powder or granules; as a solution or a suspension in an aqueous or non-aqueous liquid; or as an oil-in-water liquid emulsion or a water-in-oil liquid emulsion. Compounds I or II may also be presented as a bolus, electuary or paste.

A tablet may be made by compression or molding, optionally with one or more accessory ingredients. Compressed tablets may be prepared by compressing the compounds in a suitable machine in a free-flowing form such as a powder or granules, optionally mixed with an appropriate binder, lubricant, inert diluent, preservative, surface-active, or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredient therein using for example, hydroxypropylmethyl cellulose in varying proportions to provide the desired release profile.

Formulations suitable for parenteral administration include aqueous and non-aqueous isotonic, sterile injection solutions which may contain anti-oxidants, buffers, bacteriostats and solutes which render the formulation isotonic with the blood of the intended recipient; an aqueous and non-aqueous sterile suspensions which may include suspending agents and thickening agents. The formulations may be presented in unit-dose or multi-dose sealed containers, for example, ampules or vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above recited, or an appropriate fraction thereof, of the Compounds of the invention.

The present invention will be further described in connection with the following Examples which are set forth for the purposes of illustration only.

EXAMPLE 1

Synthesis of 1,2-O-(1-methylethylidene)-α-D-xylofuranose 3-O-(1H-imidazole-1-carbothioic acid)-4-methylbenzenesulfonic acid ester (Compound III)

A flame-dried 1 L three-necked round bottom flask equipped with a magnetic stir bar was fitted with a 250 mL pressure equalizing addition funnel and charged with a solution of 40.0 g 1,2-O-(1-methylethylidene)-α-D-xylofuranose (21.0 mmol) obtained from Pfanstiehl, in 125 ml methylene chloride. The solution was treated with 40 ml dry pyridine, then cooled to −5° C. under a nitrogen atmosphere. At this time, the addition funnel was charged with a solution of 44.2 g tosyl chloride (1.1 eq., 23.1 mmol) obtained from Aldrich in 100 ml methylene chloride. The contents of the addition funnel were added dropwise over 30 minutes to the cooled reaction mixture. After stirring overnight, during which time the reaction mixture was allowed to warm to room temperature, the contents of the flask were diluted with 500 ml methylene chloride and washed with 1×600 water, then 2×400 ml water, and finally with 1×400 ml saturated NaCl solution. The organic layer was dried over $MgSO_4$, filtered, evaporated under aspirator pressure, then further dried at 23° C./0.05 mm Hg overnight to remove residual pyridine resulting in a yield of 71 g of crude product as an off-white solid. This substance was dissolved in 100 ml methylene chloride, then treated with hexane until the solution became turbid. This mixture was stored at 0° C. overnight. The resulting solids were collected by filtration, washed well with hexane and air dried to yield 52.4 g 1,2-O-(1-methylethylidene)-5-O-p-(tolylsulfonyl)-α-D-xylofuranose as a white solid. A second crop containing 5.7 g of the desired material was collected from evaporation of the mother liquors (80% yield).

A 2 L round bottom flask equipped with a magnetic stir bar was charged with 58.1 g 1,2-O-(1-methylethylidene)-5-O-p-(tolylsulfonyl)-α-D-xylofuranose (168 mmol) and 1.0 L 1,2-dichloroethane, and then treated with 361 g thiocarbonyldiimidazole (1.2 eq., 202 mol) obtained from Fluka. The yellow solution was heated to reflux temperature for two hours, after which time TLC showed the presence of starting material. An additional 4.2 g thiocarbonyldiimidazole (0.15 eq., 23.5 mmol) was added, and heating was continued for one additional hour. The reaction mixture was cooled, and the solvent removed via rotary evaporation. The orange residue was partitioned between methylene chloride and 1.4 L water. The organic layer was separated and washed with 700 ml water, and then with 400 ml saturated NaCl solution. Drying with $MgSO_4$, filtration, and evaporation afforded 91 g. 1,2-O-(1-methylethylidene)-α-D-xylofuranose-3-O-(1H-imidazole-1-carbothioic acid)-4-methyl benzenesulfonic acid ester (Compound III) as an orange solid.

Anal. Calcd. for $C_{19}H_{22}N_2O_7S_2$ C, 50.21; H, 4.88; N, 6.16; S, 14.11. Found: C, 49.94; H, 4.85; N, 5.99; S, 13.84.

EXAMPLE 2

Synthesis of
(2S,4R)-4-(1,3-Dithian-2-yl)-1,2,4-butanetriol-1-O-(4-methylbenzenesulfonate) (Compound V)

A 2 L three-necked flask equipped with a magnetic stir bar and fitted with a 1 L pressure equalizing addition funnel was charged with 600 ml dry toluene. The solvent was degassed with argon, then heated to reflux temperature, and treated with 27.1 ml tri-n-butyltin hydride (1.5 eq. 100 mmol) obtained from Fluka, and 50 mg AIBN (Fluka). The addition funnel was charged with an argon-degassed solution containing 30.3 of the above compound (66.7 mmol) in 600 ml dry toluene. This mixture was added to the heated solution over the course of one hour. After heating an additional two hours, monitoring of the reaction by TLC showed the presence of starting material. Aliquots of 9 ml tri-n-butyltin hydride (0.5 eq., 34 mol) and 50 mg AIBN were added, and heating continued until TLC showed no starting material present (approximately one hour later). After cooling, the toluene was removed via rotary evaporation, and the residue was partitioned between 1 L acetonitrile and 800 ml hexane. The acetonitrile layer was collected and evaporated to yield 27.3 g of an off-white residue which was dissolved in a minimum volume of 30% ethyl acetate/70% hexane solution. This mixture was passed though a pad of silica gel by elution with additional 30% ethyl acetate/70% hexane solution. After evaporation of the eluant, the residue was dissolved in a minimum volume of ether, then treated with petroleum ether until the solution became turbid. Cooling in a dry ice bath, followed by storage at 0° C. overnight, and collection of the resultant solids afforded 9.3 g of 3-Deoxy-1,2-O-(1-methylethylidene)-α-D-erythro-pentofuranose-4-methylbenzene-sulfonate as a white solid. An additional 4.0 g of product was collected after evaporation of the mother liquors (61% yield).

A solution of 3-deoxy-1,2-O-(1-methylethylidene)-α-D-erthro-pentofuranose-4-methylbenzenesulfonate (12 g, 36.5 mmole) in dried methylene chloride (60 mL) was cooled to −78° C. under an atmosphere of nitrogen. To the solution was slowly added 1,3-propane-dithiol (4.0 mL, 39.8 mmole), then boron trifluoride etherate (5.0 mL, 40.6 mmole). The mixture was stirred at −78° for forty hours, at which time, the cooled mixture was diluted with methylene chloride (200 mL), washed with saturated NaCl solution (2×50 mL), dried over $MgSO_4$, filtered and evaporated. The light colored oil was purified via flash column chromatography using a 50% EtOAc/Hexane solution as eluant, which yielded 7 g of Compound V, as a colorless oil (50% yield, 90% yield based on recovered starting material). Also isolated was 5.3 g of recovered starting material.

Anal. Calcd. for $C_8H_{14}O_2S_2$: C, 46.57; H, 6.84. Found C, 46.53; H, 6.88.

EXAMPLE 3

Preparation of
(2R-trans)-tetrahydro-5-(1,3-dithian-2-yl)-3-furanol
(Compound IV(a)) and
(2R-trans)-tetrahydro-5-(1,3-dithian-2-yl)-3-furanol
.4-methylbenzenesulfonate (Compound IV(b))

A solution of Compound V (7 g., 18.5 mmole) was taken up in methylene chloride (20 mL) was treated with pyridine (4 mL, 49.5 mmole); the solution was stirred overnight, then diluted with methylene chloride (50 mL) and extracted with saturated NaCl solution (1×20 mL). The organic layer was dried over $MgSO_4$, filtered and evaporated. The residue (Compound IV(a), 5.5 g, 26.6 mmole) was redissolved in methylene chloride (10 mL), and stirred with tosyl chloride (5.5 g, 288 mmole) and pyridine (3 mL, 37.1 mmole) at room temperature overnight. Dilution with methylene chloride (100 mL), followed by washing with saturated NaCl solution (25 mL), drying over $MgSO_4$, filtration, evaporation, and chromatography (30% EtOAc/70% hexane) afforded 4.2 g (32% from acetonide starting material) of (2R)-trans-tetrahydro-5-(1,3-dithian-2-yl)-3-furanol-4-methyl-benzenesulfonate (Compound IV(b)) as a colorless oil.

EXAMPLE 4

Synthesis of (2R-trans)-tetrahydro-4-[[(4-methylphenyl)sulfonyl]oxy]-2-furannmethanol (Compound IV(c))

A mixture of (2R)-trans-tetrahydro-5-(1,3-dithian-2-yl)-3-furanol-4-methylbenzenesulfonate (1.0 g, 2.77 mmole), mercuric chloride (1.66 g, 6.1 mmole), and mercuric oxide (1.32 g, 6.1 mmole) in an 80% acetonitrile/water solution (25 mL) was warmed to 80° for 5 hours. The solution was cooled to room temperature, filtered, and partially evaporated to remove acetonitrile. The residue was diluted with 50% MeOH/water (10 mL), cooled to 0°, then treated with sodium borohydride (100 mg, 2.7 mmole). After stirring at 0° C. for fifteen minutes, the solution was concentrated, and the residue partitioned between $CH_2Cl_2$ and brine. The organic layer was collected, dried over $MgSO_4$, filtered and evaporated. The resultant oil was purified by flash column chromatography using a 60% EtOAc/40% Hexane solution as eluant to afford 530 mg (70%) of Compound IV(c) as an oil which solidified upon refrigeration: MS 241(M+—$CH_2OH$)

EXAMPLE 5

Synthesis of
(3S-trans)-tetrahydro-5-dimethoxymethyl-3-furanol
(Compound IV(d)) and
(3S-trans)-tetrahydro-5-dimethoxymethyl-3-furanol-4-methylbenzenesulfonate (Compound IV(e))

A solution of 3-deoxy-1,2-O-(1-methylethylidene)-α-D-erythro-pentofuranose-4-methylbenzenesulfonate (40 g, 0.12 mmole) in 1% (v/v) acetic acid in methanol (800 ml) was heated at 70° C. for 3 days. After cooling to room temperature the pH of the solution was adjusted to 6.0 with addition of a sodium methoxide solution. The mixture was then evaporated to dryness under vacuum to afford a foamy solid, Compound IV(d). To this substance was added 160 ml dry pyridine and tosyl chloride (50 g) and the mixture was stirred at 0° C. for 15 hours. After pouring into 400 ml ice/water, the mixture was extracted with 2×400 ml $CH_2Cl_2$ and washed with 1N HCL, $NaCHO_3$, and water, successively. The organic solution was then evaporated to dryness under vacuum to give 35.7 of a mobile liquid (93% yield).

IV(d): NMR (200 MH$_2$, CDCl$_3$)δ 2.00 (m, 2H), 3.45 (s, 6H), 3.78, 3.96 (AB of ABX, 2H, $J_{AB}=9H_z$, $J_{AX}=2H_z$, $J_{BX}=4H_z$), 4.29 (m, 2H), 4.54 (m, 1H).

Anal. Calcd for Compound IV(e), $C_{14}H_{20}O_6S$: C, 53.15, H, 6.37; N, 10.13. Found: C, 53.18; H, 6.25; N, 10.10.

EXAMPLE 6

Synthesis of (2R-trans)-tetrahydro-4-[[(4-methylphenyl)
sulfonyl]oxy]-2-furanmethanol (Compound IV(c))

A mixture of (3S-trans)-tetrahydro-5-(dimethoxymethyl)-3-furanol-4-methylbenzenesulfonate, (Compound IV(e), 10.0 g, 31.6 mmole), 1% $CF_3CO_2H$ (50 mL), and dioxane (80 mL) in a 250 mL round bottom flask fitted with a reflux condenser was warmed to 80° C. for five hours. After cooling to room temperature, the solution was adjusted to pH 7.0 using 1N NaOH, treated with $NaBH_4$ (1.2 g, 31.7 mmole), and allowed to stir at room temperature for an additional 30 minutes. The solvent was partially removed, then extracted with EtOAc (100 mL×3). The organic fraction was dried over MgSO4, filtered, evaporated and purified by flash column chromatorgraphy (60% EtOAc/40% Hexane) to afford 3.6 g or recovered starting material and 2.7 g (49% based on recovered starting material) of Compound IV(c).

EXAMPLE 7

Synthesis of
(2R-cis)-4-(6-Amino-9H-purin-9-yl)tetrahydro-2-furanmethanol (Compound I)

To a flame-dried argon blanketed round bottom flask equipped with a magnetic stir bar and condenser was added adenine (50 mg, 0.37 mmole) $K_2CO_3$ (100 mg, 0.73 mmole), 18-crown-6 (97 mg, 0.37 mmole) and DMF (10 mL). This mixture was allowed to stir at room temperature for 30 minutes under a stream of argon. A solution of (2R-trans)-tetrahydro-4-[[(4-methylphenyl)-sulfonyl]oxy]-2-furanmethanol, Compound IV(c), (100 mg, 0.37 mmole) in 2 mL DMF was then added dropwise to the stirring mixture. The resultant mixture was warmed to 80° C., and stirred at that temperature overnight. After removal of the solvent in vacuo, the solid residue was purified by flash chromatorgraphy using a 10% MeOH/90% $CH_2Cl_2$ solution as eluent. This isolated material was further purified by reverse-phase HPLC using a gradient elution system of $CH_3CN/H_2O$ to yield 25 mg (29%) of Compound I as a white solid. An analytical sample was crystallized from methanol: mp 183°–185°, $[\alpha]_D+47.91$ (c 0.67, MeOH).

UV λ max (MeOH) 260 nm (ε 13990); UV λ max (pH 1) 210 nm (ε 19700), 259 nm (ε 13600);

EXAMPLE 8

Synthesis of
(3R-cis)-9-[tetrahydro-5-(dimethyoxymethyl)-3-furanyl]-9H-purin-6-amine (Compound VI)

To a flame-dried argon blanketed round bottom flask equipped with a magnetic stir bar and condenser was added adenine (2.14 g, 15.8 mmole), $K_2CO_3$ (4.37 g, 31.6 mmole), 18-crown-6 (417 mg, 1.58 mmole) and DMF (400 mL). This mixture was allowed to stir at room temperature for 30 minutes under a stream of argon. A solution of (3S-trans)-tetrahydro-5-(dimethoxymethyl)-3-furanol-4-methylbenzenesulfonate. Compound IV(e), (5.0 g, 15.8 mmole) in 100 mL DMF was then added dropwise to the stirring mixture; the resultant mixture was warmed to 80° C., and stirred at that temperature overnight. Filtration, followed by evaporation of DMF, afforded a solid residue. This material was passed through a silica gel pad using a 7% MeOH/93% $CH_2Cl_2$ solution as eluant. Fractions containing the desired product were collected and evaporated to yield 3.0 g (71%) of Compound VI as a white solid:

mp 144°–146°; UV λ max (MeOH) 214 nm (ε 18890), 258 nm (ε 14100); UV λ max (pH1) 208 nm (ε 20000) 258 nm (ε 13780); UV λ max (pH 13) 259 nm (ε 14120).

EXAMPLE 9

Synthesis of
(2R-cis)-4-aminotetrahydro-2-furanmethanol
(Compound IV(f))

A solution of (2R-trans)-tetrahydro-4-[[(4-methylphenyl) sulfonyl]oxy]-2-furanmethanol, Compound IV(c), (150 mg, 0.55 mmole) in predried DMF (3 mL) was cooled to −5° C., and treated with $NaN_3$ (90 mg, 1.38 mmole). The solution was allowed to warm to room temperature, then heated at 70° C. for five hours. After removal of DMF, the residue was partitioned between EtOAc (50 mL) and $H_2O$ (10 mL). The organic layer (10 mL). The aqueous layers were combined, and backwashed with EtOAc (50 mL×3). All organic fractions were pooled, and dried over MgSO$_4$, filtered and evaporated. This material was combined with pre-dried MeOH (5 mL) and 10% Pd on carbon (15 mg) in a flame-dried 25 mL round bottom flask. The flask was blanketed with H$_2$, and allowed to stir at room temperature for three hours. The catalyst was removed via filtration, and the solvent evaporated to provide 54 mg (84%) of (2R-cis)-4-aminotetrahydro-2-furanmethanol as a colorless oil which required no further purification: MS 99(M+—H$_2$O).

EXAMPLE 10

Synthesis of (2R-cis)-4-[(5-amino-6-chloro-4-pyrimidinyl) amino]tetrahydro-2-furanmethanol (Compound IX)

To a 50 mL round bottom flask fitted with a reflux condenser was added (2R-cis)-4-aminotetrahydro-2-furanmethanol, Compound IV(f), (184 mg, 1.57 mmole), 5-amino-4,6-dichloro-pyrimidine (770 mg, 4.70 mmole), triethylamine (0.44 mL, 3.16 mmole) and t-butyl alcohol (16 mL). The reaction mixture was heated to reflux temperature under an atmosphere of argon for 72 hours, at which time the volatile materials were removed by rotary evaporation. The residue was dissolved in 100 mL EtOAc, washed with saturated NaHCO$_3$ solution (50 mL) and saturated NaCL solution (50 mL), then dried over MgSO$_4$. After filtration and evaporation, the product was purified by flash column chromatography (50% EtOAc/50% Hexane) to yield 220 mg (58%) of Compound IX.

UV λ max (MeOH) 206 nm, 265 nm, 295 nm; UV λ max (pH 1) 204 nm, 304 nm.

EXAMPLE 11

Synthesis of (2R-cis)-4-(6-chloro-9H-purin-9-yl) tetrahydro-2-furanmethanol (Compound X)

A solution of (2R-cis)-4-[(5-amino-6-chloro-4-pyrimidinyl)amino]tetrahydro-2-furanmethanol, Compound IX, (220 mg, 0.90 mmole) and diethoxymethylacetate (5 mL) in a 10 mL round bottom flask fitted with a reflux condenser was heated to 100° for 120 hours. The volatile materials were removed via rotary evaporation, and the residue was recombined with toluene (5 mL) and p-toluenesulphonic acid (5 mg). After stirring at room temperature for one hour and by flash column chromatography (10% MeOH/90% CH$_2$Cl$_2$) to afford 109 mg (48%) of Compound X as a white solid:

UV λ max (MeOH) 264 nm; UV λ max (pH1) 265 nm;

EXAMPLE 12

Synthesis of (2R-cis)-4-(6-amino-9H-purin-9-yl)tetrahydro-2-furanmethanol (Compound I) and (2R-cis)-tetrahydro-4-(6-methoxy-9H-purin-9-yl)-2-furnamethanol (Compound XI)

A solution of (2R-cis)-4-(6-chloro-9H-purin-9-yl) tetrahydro-2-furanmethanol (73 mg, 0.28 mmole) in 16% NH$_3$/methanol (15 mL) was sealed in a stainless steel bomb and allowed to react for 96 hours. Evaporation of the solution, followed by flash column chromatography (10% MeOH/90% CH$_2$Cl$_2$) afforded Compound I (20 mg, 29%) and Compound XI (38 mg. 53%) as a white solid.

XI: UV λ max (MeOH) 249 nm; UV λ max (pH1) 250 nm.

EXAMPLE 13

Synthesis of (2R-cis-4-(2-amino-6-chloro-9H-purin-9-yl) tetrahydro-2-furanmethanol (Compound VIII)

To a flame-dried argon blanketed round bottom flask equipped with a magnetic stir bar and condenser was added 2-amino-6-chloro-purine (63 mg, 0.37 mmole), K$_2$CO$_3$ (100 mg, 0.73 mmole), 18-crown-6 (97 mg, 0.37 mmole) and DMF (10 mL). This mixture was allowed to stir at room temperature for 60 minutes under a stream of argon. A solution of (2R-trans)-tetrahydro-4-[(4-methylphenyl)sulfonyl]oxy-2-furanmethanol (100 g, 0.37 mmole) in 2 mL DMF was then added dropwise to the stirring mixture; the resultant mixture was warmed to 80° C., and stirred at that temperature overnight. After removal of the solvent in vacuo, the solid residue was purified by flash chromatography using a 5% MeOH/95% CH$_2$Cl$_2$ solution as eluent. The isolated material was further purified by reverse-phase HPLC using a gradient elution system of CH$_3$CN/H$_2$O to yield 30 mg (30%) of Compound VIII as a white solid: UV λ max (EtOH) 221 nm, 240 nm, 303 mm.

EXAMPLE 14

Synthesis of (2R-cis-4-(6-Amino-9H-purin-9-yl)tetrahydro-2-furan-carbaldehyde (Compound VIII) and (2R-cis-4-(6-Amino-9H-purin-9-yl) tetrahydro-2-furanmethanol (Compound I)

A solution of (3R-cis)-9-[tetrahydro-5-(dimethoxymethyl)-3-furanyl]-9H-purin-6-amine (4.35 g, 16.3 mmole) in a 0.1 oxalic acid solution (200 mL) was heated at reflux temperature for 18 hours to give VII. After cooling to room temperature, the solution containing Compound XII was neutralized with 1N NaOH solution. The resultant mixture was combined with PtO$_2$ (50 mg, cat.), and stirred under an atmosphere of hydrogen for 48 hours. Filtration, evaporation and purification via flash column chromatography (5% MeOH/95% CH$_2$Cl$_2$) afforded 2.0 g (52%) of Compound I as a white solid. If necessary, the product can be further purified by recrystallization form MeOH.

EXAMPLE 15

Synthesis of (3R-cis-2-Amino-1,9-dihydro-9-[tetrahydro-5-(hydroxymethyl)-3-furanyl]-6H-purin-6-one (Compound II)

A solution of (2R-cis)-4-(2-amino-6-chloro-9H-purin-9-yl)-tetrahydro-2-furanmethanol (170 mg, 0.63 mmole) in 1N HCl (25 mL) was heated to reflux temperature for three hours. The reaction mixture was neutralized with 40% KOH solution, then evaporated to afford a white solid. Purification via reverse-phase HPLC using a CH$_3$CN/H$_2$O gradient elution system provided 65 mg (41%) of II as a white solid: mp=229°–230°; UV λ max (pH 0) 205 nm, 253 nm, 278 nm; UV λ max (pH 6) 252 nm, 270 nm; UV λ max (pH 13) 255 nm, 268 nm.

EXAMPLE 16

Synthesis of Compound II via Compounds XII and XIII

To a 25 mL round bottom flask fitted with a reflux condenser was added (2R-cis)-4-Aminotetrahydro-2-furanmethanol (427 mg, 3.64 mmole), triethylamine (3.5 mL, 25 mmole) and DMF (5 ml). The reaction mixture was heated to 60° C. for 6 hours, at which time tlc showed the disappearance of starting material. After cooling to room temperature, the reaction mixture was concentrated in the presence of silica gel by rotary evaporation. The resultant absorbed material was loaded onto a silica gel column (approximately 300 mL) and eluted with a 5:1 $CH_2Cl_2$/MeOH solution, then a 3:1 $CH_2Cl_2$/MeOH solution to provide 730 mg (94%) of the desired product, Compound XII. Compound XII (200 mg, 0.7 mmole) was combined with $PtO_2$ (75 mg, cat.) and 50 mLs of a 1:3 (v/v) solution of formic acid and MeOH. This mixture was hydrogenated at 55 p.s.i. for 48 hrs. Filtration followed by evaporation afforded XIII. This residue was combined with DMF (5 mL) triethylorthoformate (5 mL) and p-toluenesulphonic acid (200 mg, cat) and heated to 80° C. for 4 hours. The solution was then evaporated and recombined with 10 mL 0.5N HCl and stirred for an additional 4 hours. After neutralization, the mixture was evaporated and purified to give II.

EXAMPLE 17

Testing of Compounds I and II for anti-HIV Activity

Compounds I and II were tested in the HIV-cytopathic Effect Inhibition Assay as described in the publication by Mitsuya, et al. *Proc. Nat'l Acad. Sci., USA.* 83:1911 (1986), which publication is hereby incorporated by reference.

The cells were exposed to either Compound I, Compound II, or AZT, and the survival of drug treated target cells determined seven days thereafter.

Figure 1:
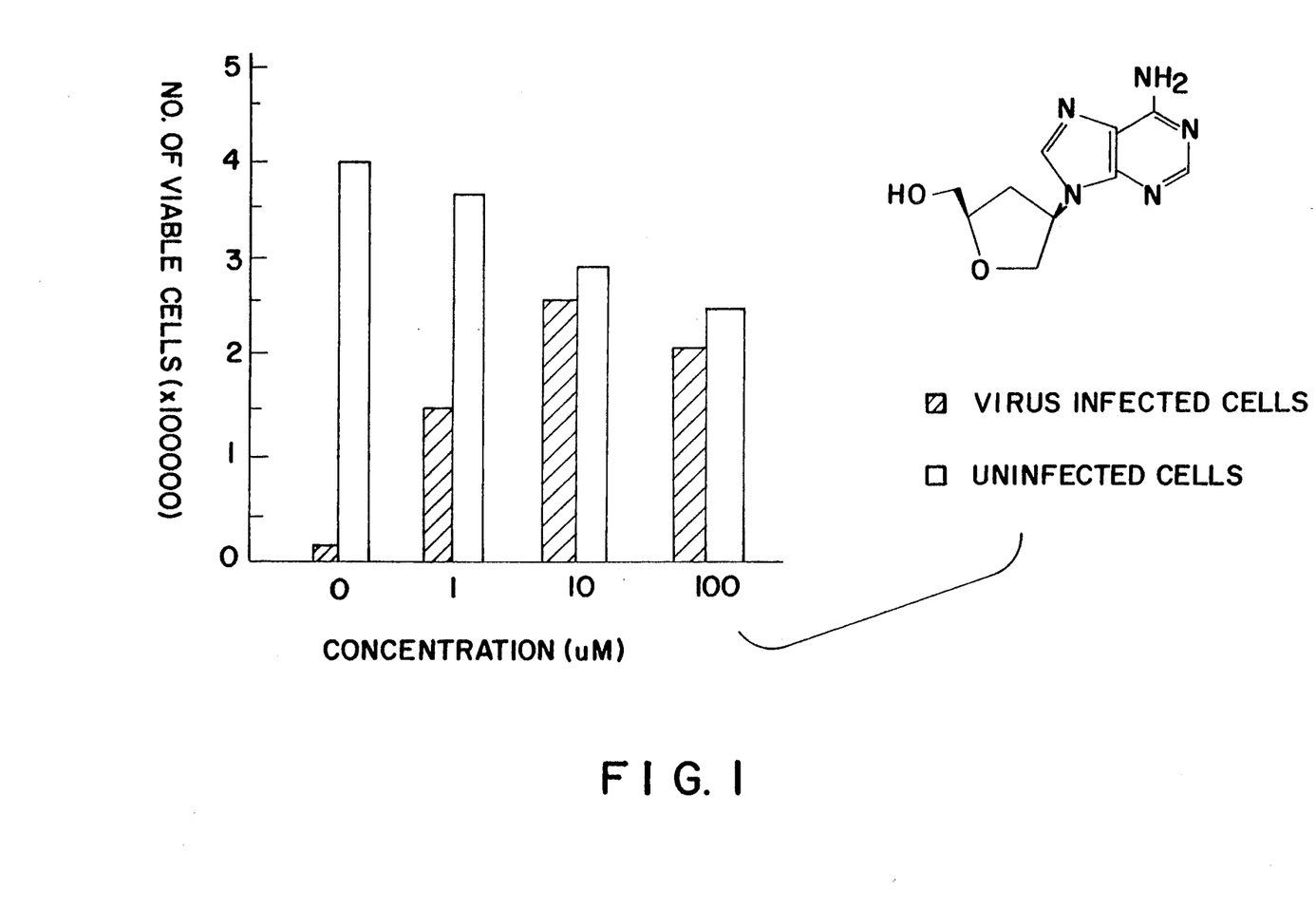
FIGS. 1 through 3 summarizes the results of testing the compounds of this invention for anti I-HIV activity as against AZT.
Figure 2:
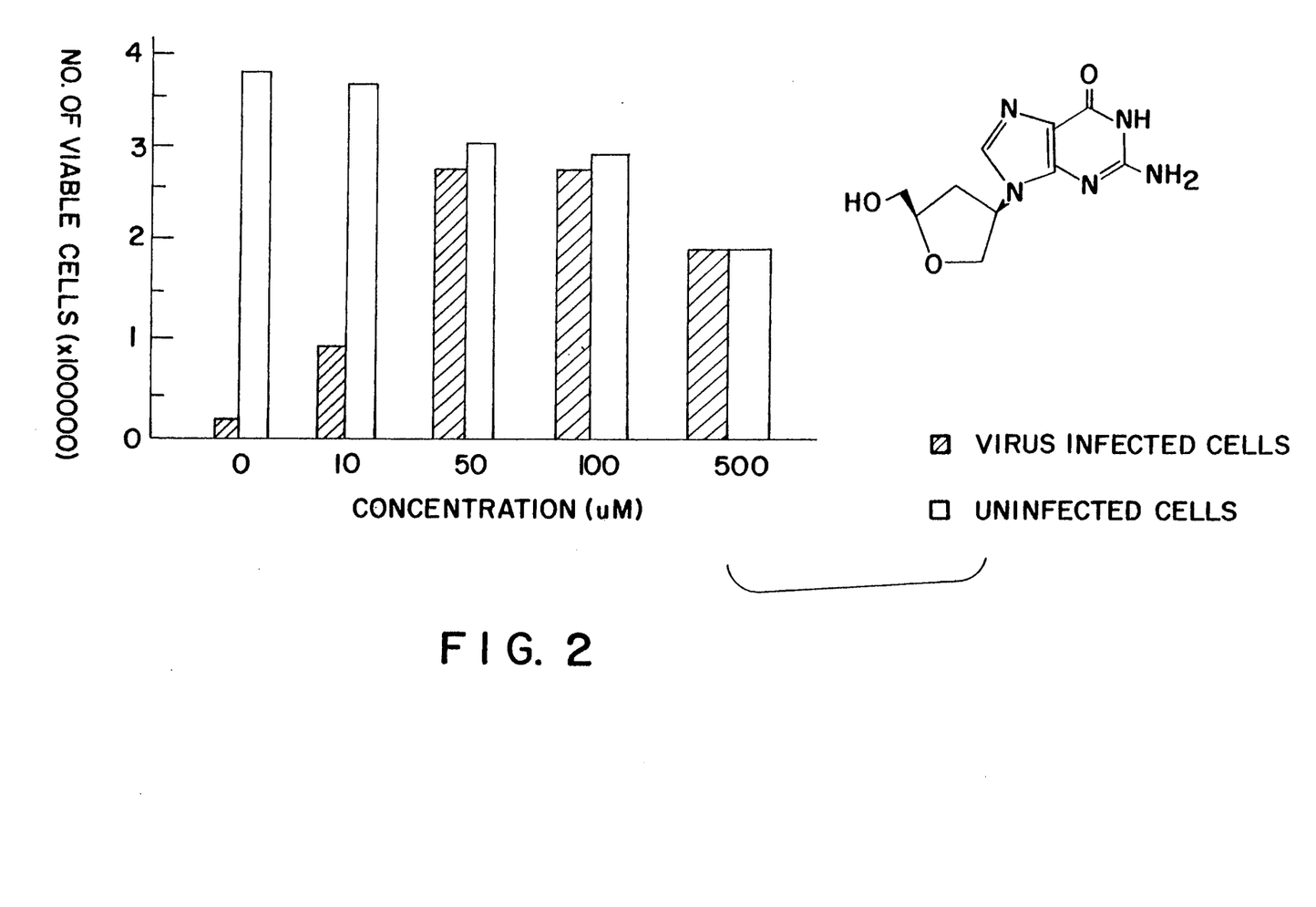
Figure 3:
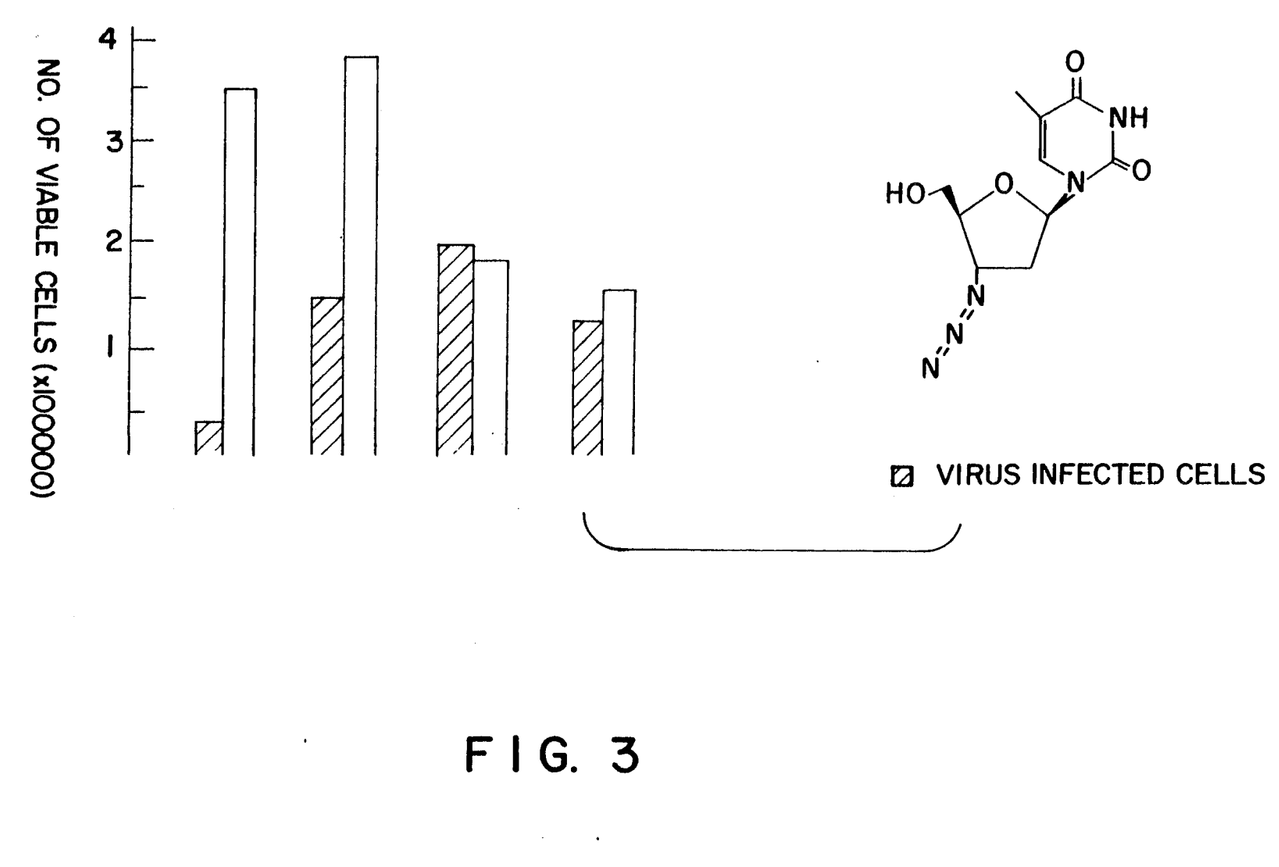

The results are summarized in FIGS. 1 to 3. The black bars represent survival of compound treated target cells when HIV (HTLV-III) is added. The light bars represent survival of compound treated target cells in the absence of virus.

Compounds I and II exhibit anti-HIV activity equivalent to that of antiretroviral therapeutics known to have in vivo activity against HIV, most particularly AZT.

EXAMPLE 18

Testing of Compounds I and II for anti-HIV activity in ELISA test systems

The Enzyme Linked Immuno-absorbent Assay (ELISA) was used to test compounds I and II for anti-HIV activity by measuring virus growth in CD4+ T-lymphocytes by detecting antigen released into the tissue culture supernatant of infected cells.

MATERIALS AND METHODS

Preparation of Samples for Antigen ELISA

High titre virus stocks [HIV, HTLV III; RF strain] were grown in H9 cells in RPMI 1640 (Flow Laboratories) supplemented with 10% fetal calf serum, penicillin (100 IU/ml) and streptomycin (100 ug/ml). Cell debris was removed by low speed centrifugation and the supernatant stored at −70° C. until required. The host cell line used in the antiviral assays was the C8166 CD4+ T-cell line which is particularly susceptible to infection with HIV. Cells were incubated with 10 T-cell line which is particularly susceptible to infection with HIV. Cells were incubated with 10 $TCID_{50}$, HIV/HTLV III(RF) at 37° C. for 90 minutes and then washed three times with PBSA. Cell aliquots ($2 \times 10^5$) were resuspended in 1.5 ml growth medium in 6 ml tubes and incubated at 37° C. At 72 hours post-infection, the supernatants from the cell cultures were assayed immediately for HIV antigen.

HIV antigen Capture ELISA

The antigen capture ELISA used was purchased from Coulter (Luton, UK). The assays were carried out on supernatants taken from infected cell cultures using the steps described by the manufacturers. In each assay the corresponding positive and negative internal controls were included together with a supernatant control taken from uninfected cells. The plates were read using the appropriate spectrophotometric detection system.

Results

The ELISA testing of Compound I and ddA (which is a known anti-HIV agent) is set forth below.

| $IC_{50}$ (uM) | Compound |
|---|---|
| 3-10 | I |
| 1-3 | ddA |

Compound I has antiviral activity in this test system, comparable to that of a known anti-HIV agent ddA.

EXAMPLE 19

| Tablet Formulations for Compounds I and II | |
|---|---|
| Ingredients | mg/tablet |
| A. 0.05 mg Tablet | |
| 1. Compound I or Compound II | 0.05 |
| 2. Lactose, Anhydrous | 94.00 |
| 3. Iron Oxide Black | 0.15 |
| 4. Microcrystalline cellulose (Avicel PH-102) | 25.00 |
| 5. Croscarmellose Sodium, Type A (Ac-Di-Sol) | 5.00 |
| 6. Magnesium Stearate | 0.80 |
| TOTAL | 125.00 mg |
| B. 2 mg Tablet | |
| 1. Compound I or Compound II | 2.00 |
| 2. Lactose, Anhydrous | 147.00 |
| 3. Cosmetic Iron Oxide Yellow | 0.40 |
| 4. Microcrystalline Cellulose (Avicel PH-102) | 40.00 |
| 5. Croscarmellose Sodium, Type A (Ac-Di-Sol) | 8.40 |
| 6. Magnesium Stearate | 2.20 |
| TOTAL | 200.00 mg |

EXAMPLE 20

| Injectable Formulations for Compounds I and II | |
|---|---|
| A. Sterile Powder for Injection | |
| 1. Compound I or Compound II Lyophilized Powder, 10 mg/Vial | |
| Ingredients | mg/vial |
| 1. Compound I or Compound II | 10.00 |
| 2. Mannitol | 50.00 |
| 3. Hydrochloric Acid (1% v/v) | |
| 4. Water for Injection | |
| B. Compound I or Compound II Lyophilized Powder, 100 mg/Vial | |
| Ingredients | mg/vial |
| 1. Compound I or Compound II | 100.00 |
| 2. Mannitol | 50.00 |
| 3. Hydrochloric Acid (1% v/v) | |
| 4. Water for Injection | |
| C. Powder for Reconstitution | |
| 1. Compound I or Compound II 0.5 mg Powder | |

-continued

| Injectable Formulations for Compounds I and II | |
|---|---|
| Ingredients | mg |
| 1. Compound I or Compound II | 0.50 |
| 2. Lactose, Anhydrous | 99.50 |
| TOTAL | 100.00 mg | a The Hydrochloric Acid Solution is used to adjust the pH of the bulk solution prior to lyophilization.
b. The Water for Injection is essentially volatilized during lyophilization.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A compound of the formula:

wherein A is 6-Amino-9H-purin-9-yl or 2-amino-6-hydroxy-9H-purin-9-yl, wherein the amino group may be replaced by and N=CHR³R⁴, and R is OH or wherein $R^1$, $R^2$, $R^3$ and $R^4$ is each independently straight or branched chain $C_{1-20}$ alkyl, $C_{1-12}$ alkoxyalkyl, substituted or unsubstituted phenoxyalkyl ($C_{1-4}$), substituted or unsubstituted phenyl with the substituents selected from the group consisting of halogen, $C_{1-4}$ alkoxy, nitro, hydroxy, carboxyl or alkylamino, and the pharmaceutically acceptable salts thereof.

2. The compound of claim 1 wherein A is unsubstituted 6-amino-9H-purin-9-yl.

3. The compound of claim 2 wherein R is OH said compound having the formula:

I

4. The compound of claim 1 wherein A is unsubstituted 2-amino-6-hydroxy-9H-purin-9-yl.

5. The compound of claim 4 wherein R is R is OH said compound having the formula:

II

6. A method for treating a retroviral infection in a subject comprising treating the subject with an antivirally effective amount of the compound of claim 1.

7. The method of claim 4 wherein the retroviral infection is AIDS.

8. A compound of the formula:

VI

9. A compound of the formula:

VII

10. A compound of the formula:

VIII

11. A compound of the formula:

X

12. A compound of the formula:

XI

13. A pharmaceutical composition comprising a minor amount of Compound I and a major amount of pharmaceutically acceptable carriers.

14. A pharmaceutical composition comprising a minor amount of Compound II and a major amount of pharmaceutically acceptable carriers.

15. A method for treating cells infected with a retrovirus comprising, treating the cells with an antivirally effective amount of the compound of claim 1.

16. A method as recited in claim 15 wherein the cells are infected with HIV.

* * * * *